United States Patent
Jones et al.

(10) Patent No.: US 7,333,844 B2
(45) Date of Patent: Feb. 19, 2008

(54) UTERINE TISSUE MONITORING DEVICE AND METHOD

(75) Inventors: Michael L. Jones, San Clemente, CA (US); Jill Uyeno, Mission Viejo, CA (US); Fred H. Burbank, Laguna Niguel, CA (US); Greig E. Altieri, Laguna Beach, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 597 days.

(21) Appl. No.: 10/402,892

(22) Filed: Mar. 28, 2003

(65) Prior Publication Data

US 2004/0193028 A1 Sep. 30, 2004

(51) Int. Cl.
*A61B 5/05* (2006.01)
*A61B 5/00* (2006.01)

(52) U.S. Cl. ...................... 600/361; 600/364
(58) Field of Classification Search ........... 600/361, 600/364
See application file for complete search history.

(56) References Cited

U.S. PATENT DOCUMENTS

| | | | |
|---|---|---|---|
| 2,168,867 A * | 8/1939 | George ............. 600/350 |
| 2,400,251 A | 5/1946 | Nagel | |
| 3,123,067 A * | 3/1964 | Clark, Jr. .......... 600/361 |
| 3,209,753 A | 10/1965 | Hawkins et al. | |
| 3,411,505 A | 11/1968 | Nobis | |
| 3,777,740 A | 12/1973 | Hokanson | |
| 3,973,555 A * | 8/1976 | Moller et al. ....... 600/348 |
| 4,292,960 A | 10/1981 | Paglione | |
| 4,428,374 A | 1/1984 | Auburn | |
| 4,428,379 A | 1/1984 | Robbins et al. | |
| 4,440,620 A * | 4/1984 | Ono et al. ......... 204/403.1 |
| 4,509,528 A | 4/1985 | Sahota | |
| 4,546,436 A * | 10/1985 | Schneider et al. ...... 600/361 |
| 4,618,929 A * | 10/1986 | Miller et al. ......... 600/348 |
| 4,650,466 A | 3/1987 | Luther | |

(Continued)

FOREIGN PATENT DOCUMENTS

| DE | 195 28 440 A | 2/1997 |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |

(Continued)

OTHER PUBLICATIONS

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

(Continued)

*Primary Examiner*—Charles A. Marmor, II
*Assistant Examiner*—Patricia Mallari (57) ABSTRACT

The invention provides a devices, methods and systems to measure and record uterine tissue environment components such as pH during the course of uterine artery occlusion. The uterus becomes ischemic due to the occlusion thereof, and its pH drops sharply within minutes of uterine artery occlusion and remains relatively low for a period of time. The return of normal pH is an indicator of return of blood to the ischemic tissue. In use, a catheter with a pH measuring tip is advanced through the patient's vaginal canal and into the patient's uterine cavity until the pH measuring active electrode on the distal end of the catheter contacts or penetrates the uterine fundus. The active electrode detects the pH and a signal representing pH is transmitted to a pH recording and monitoring device which preferably displays the pH. The signal may be transmitted through a conductor or by a radio transmitter. Components other than pH may be monitored such a $pCO_2$, and $pO_2$.

59 Claims, 3 Drawing Sheets

U.S. PATENT DOCUMENTS

| | | | |
|---|---|---|---|
| 4,757,823 A | 7/1988 | Hofmeister et al. | |
| 4,945,896 A | 8/1990 | Gade | |
| 4,991,588 A | 2/1991 | Pflueger et al. | |
| 4,994,069 A | 2/1991 | Ritchart et al. | |
| 5,037,430 A | 8/1991 | Hasson | |
| 5,037,433 A | 8/1991 | Wilk et al. | |
| 5,050,297 A * | 9/1991 | Metzger | 29/855 |
| 5,081,997 A | 1/1992 | Bosley, Jr. et al. | |
| 5,105,812 A * | 4/1992 | Corman | 600/350 |
| 5,108,408 A | 4/1992 | Lally | |
| 5,201,314 A | 4/1993 | Bosley et al. | |
| 5,226,911 A | 7/1993 | Chee et al. | |
| 5,261,409 A | 11/1993 | Dardel | |
| 5,275,166 A | 1/1994 | Vaitenkunas et al. | |
| 5,289,831 A | 3/1994 | Bosley | |
| 5,336,229 A | 8/1994 | Noda | |
| 5,336,231 A | 8/1994 | Adair | |
| 5,383,922 A | 1/1995 | Zipes et al. | |
| 5,456,693 A | 10/1995 | Conston et al. | |
| 5,458,596 A | 10/1995 | Lax et al. | |
| 5,488,958 A | 2/1996 | Topel et al. | |
| 5,496,331 A | 3/1996 | Xu et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,570,692 A | 11/1996 | Morinaga | |
| 5,588,960 A | 12/1996 | Edwards et al. | |
| 5,596,988 A * | 1/1997 | Markle et al. | 600/353 |
| 5,598,841 A | 2/1997 | Taniji et al. | |
| 5,614,204 A | 3/1997 | Cochrum | |
| 5,658,299 A | 8/1997 | Hart | |
| 5,662,676 A | 9/1997 | Koninckx | |
| 5,662,680 A | 9/1997 | Desai | |
| 5,665,096 A | 9/1997 | Yoon | |
| 5,672,153 A | 9/1997 | Lax et al. | |
| 5,672,172 A | 9/1997 | Zupkas | |
| 5,691,314 A | 11/1997 | Hodgen | |
| 5,697,942 A | 12/1997 | Palti | |
| 5,702,407 A | 12/1997 | Kaji | |
| 5,713,371 A | 2/1998 | Sherman et al. | |
| 5,713,896 A | 2/1998 | Nardella | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,749,879 A | 5/1998 | Middleman et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,895,395 A | 4/1999 | Yeung | |
| 5,899,861 A | 5/1999 | Friemel et al. | |
| 5,904,651 A | 5/1999 | Swanson et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,941,889 A | 8/1999 | Cermak | |
| 5,979,453 A | 11/1999 | Savage et al. | |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,039,693 A | 3/2000 | Seward et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,080,118 A | 6/2000 | Blythe | |
| 6,096,051 A | 8/2000 | Kortenbach et al. | |
| 6,106,473 A | 8/2000 | Violante et al. | |
| 6,169,914 B1 | 1/2001 | Hovland et al. | |
| 6,175,751 B1 | 1/2001 | Maizes | |
| 6,186,947 B1 | 2/2001 | Ouchi | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,368,340 B2 | 4/2002 | Malecki et al. | |
| 6,425,867 B1 | 7/2002 | Vaezy et al. | |
| 6,689,056 B1 * | 2/2004 | Kilcoyne et al. | 600/300 |
| 6,905,506 B2 | 6/2005 | Burbank et al. | |
| 2002/0165579 A1 | 11/2002 | Burbank et al. | |
| 2002/0183771 A1 | 12/2002 | Altieri et al. | |
| 2003/0120306 A1 | 6/2003 | Burbank et al. | |

FOREIGN PATENT DOCUMENTS

| | | |
|---|---|---|
| EP | 1 072 282 | 1/2001 |
| FR | 1 220 773 A | 5/1960 |
| GB | 2 302 025 A | 1/1997 |
| GB | 2 311 468 A | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 02/39904 A1 | 5/2002 |
| WO | WO 02/078521 | 10/2002 |

OTHER PUBLICATIONS

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50(7-8):337-339 (1998).

Brohim, Robert M. et al., "Development of Independent Vessel Security After Ligation With Absorbable Sutures or Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US03/35815 mailed Jun. 30, 2004.

International Search Report for PCT/US2004/038111, mailed May 3, 2005.

Written Opinion for PCT/US2004/038111, mailed May 3, 2005.

Translation of FR 1 220 773.

* cited by examiner

UTERINE TISSUE MONITORING DEVICE AND METHOD

FIELD OF THE INVENTION

The invention relates generally to diagnostic measurements during the treatment of uterine disorders by the reduction of blood flow through a female patient's uterine artery.

BACKGROUND OF THE INVENTION

Hysterectomy (surgical removal of the uterus) is performed on approximately 600,000 women annually in the United States. Hysterectomy is often the therapeutic choice for the treatment of a variety of uterine disorders such as cancer, adenomyosis, menorrhagia, uterine prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Newer treatment methods have been developed for some diseases which avoid the need for a hysterectomy. For example, in 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is known as "uterine artery embolization". In this technique, uterine arteries are accessed via a transvascular route from a common femoral artery into the left and right uterine arteries. The technique uses standard interventional radiology angiographic techniques and equipment, whereby the uterine arteries are accessed via a transvascular route from a common femoral artery into the left and right uterine arteries. Uterine artery embolization can be effectively used to control uterine bleeding from a variety of sources using coils placed in arterial and venous lumens (See U.S. Pat. Nos. 4,994,069, 5,226,911, and 5,549,824, all of which are incorporated in their entireties herein), or particles (GELFOAM pledgets, available from Upjohn, Kalamazoo, Michigan, or IVALON particles, available from Boston Scientific).

One of the key features for treating fibroids with uterine artery embolization is the fact that fibroids live a tenuous vascular life with very little ability to recruit a new blood supply from the host when the primary blood supply is compromised. The uterus on the other hand has a dual (or redundant) blood supply; the primary blood supply is from the bilateral uterine arteries, the secondary blood supply from the bilateral ovarian arteries. Consequently, when both uterine arteries are occluded, i.e., bilateral vessel occlusion, the uterus and the fibroids contained within the uterus are both deprived of their blood supply. However, as demonstrated by Ravina et al., the effect on the fibroids is greater than the effect on the uterus. In most instances, the fibroids wither and cease to cause clinical symptoms.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms. See also Burbank, et al., "Uterine Artery Occlusion by Embolization or Surgery for the Treatment of Fibroids: A Unifying Hypothesis- Transient Uterine Ischemia," The Journal of the American Association of Gynecologic Laparoscopists, November 2000, Vol. 7, No.4 Supplement, pp. S3-S49. U.S. Pat. No. 6,254,601, to Burbank et al. entitled "Methods for Occlusion of the Uterine Arteries," describes numerous devices and methods useful for occluding a uterine artery.

The current treatments offered to women for fibroid treatment or uterine bleeding focus on permanent or near permanent occlusion methods for the uterine artery. For example, embolizing with PVA particles causes uterine artery occlusion for 6 months to permanent in situ); embolizing with stainless steel coils causes permanent occlusion; embolizing with Gelfoam occludes for 3 to 4 weeks before degradation of the embolic particles; surgical ligation with metal vascular clips occlude permanently; and surgical ligation with RF ablation results in permanent occlusion.

The prior art devices and methods are therefore aimed at permanent occlusion of the uterine artery, resulting in redirection of the blood flow to the uterus through collateral circulation. The patients who suffer most dramatically from uterine myomata are women of child bearing age who may desire to bear additional children. The current methods of embolizing or ligating uterine arteries are specifically contraindicated for women who desire to bear additional children. This is the realization of inadequate blood supply to the uterus because of the loss of the uterine arteries, the primary blood supply. While there have been reports of women who have undergone uterine artery embolization with PVA particles and who have subsequently become pregnant and deliver normal babies. Women who have undergone uterine artery embolization have also experienced premature menopause due to ovarian failure.

Recent advances in non-permanent occlusion of uterine arteries for treating a variety of uterine disorders have relied upon time period to determine when to re-establish blood flow through the patient's uterine artery. However, the duration of the uterine artery occlusion does not always provide an accurate assessment of the treatment for a particular disorder, particularly uterine fibroids.

SUMMARY OF THE INVENTION

The invention is directed to the detection of the extent of uterine artery occlusion in the treatment of uterine disorders in a female patient, and specifically, to monitoring of ionic components of the patient's uterine tissue such as the endometrium and myometrium.

Occlusion of the uterine arteries alters the chemical environment of uterine tissue in a time dependent fashion, typically in three phases, an initial phase, a dwell phase and a return phase. Before the occlusion of the uterine arteries, the pH of the uterine tissue can range from about 6.0 to about 7.5, usually about 6.3 to about 7.0. Upon the occlusion of the patient's uterine arteries, the pH of the tissue begins to decline, the initial phase, as soon as it becomes ischemic which is a few minutes (typically about 2 to about 120 minutes, usually about 10 to about 60 minutes). The pH of the uterine tissue declines in the initial phase about 0.2 to about 1.0. pH units, usually about 0.3 to about 0.7 pH units. The pH stays at a lower level, the dwell phase, for about 10 to about 120 minutes, typically about 10 to about 80 minutes. After the dwell phase, the pH returns to normal or near normal pH values that existed prior to the uterine artery occlusion which is the return phase. The initial phase can last about 10 to about 90 minutes, but typically last about 10 to about 60 minutes. The increase of the uterine tissue pH after uterine artery occlusion is usually an indication that the ischemic tissue is receiving blood flow from collateral arteries such as the ovarian arteries, if the uterine arteries remain occluded. While the discussion herein refers primarily directed to monitoring the pH of uterine tissue, other species may be monitored such as $pCO_2$, and $pO_2$. Other components of the uterine tissue environment may be measured in the same or similar fashion. With pH monitoring the initial phase is a descent phase and the return phase is an ascent phase. When other components are monitored, the initial phase may be an ascent phase while the return phase is a descent phase.

The time for effective uterine artery occlusion treatments may vary from patient to patient depending on a variety of factors, including the amount of collateral blood flow from the patient's ovarian and other arteries. However, the short term pH changes in the patient's uterine tissue, which result from the uterine artery occlusion, provide a more accurate indication of the progress of the procedure than existing methods.

These and other advantages of the invention will be evident from the following detailed description of the invention hen taken in conjunction with the attached exemplary drawing.

DETAILED DESCRIPTION OF THE INVENTION

Figures 1, 2, 3:
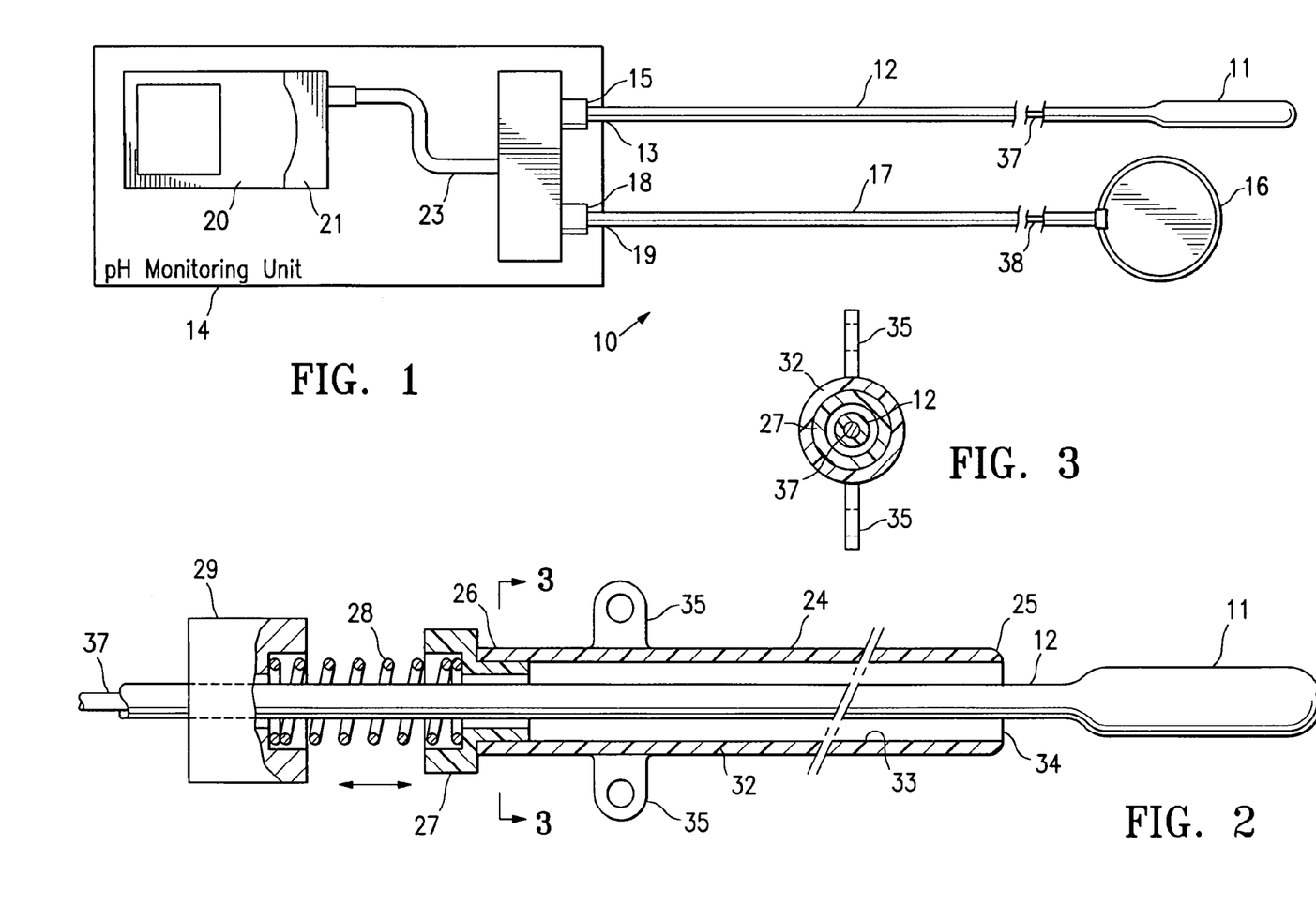
FIG. 1 is a schematic elevational view of the component monitoring system embodying features of the invention.
FIG. 2 is an enlarged elevational view of the monitoring system illustrating the sheath and biasing mechanism for urging the operative end of the monitor against the endometrium surface within the patient's uterine cavity.
FIG. 3 is a partial transverse cross-sectional view of the system shown in FIG. 2 taken along the lines 3-3.

FIG. 1 illustrates a component monitoring system 10 embodying features of the invention which includes a permeable distal antimony electrode 11, an elongated shaft 12 having a proximal end 13 secured to a pH monitoring unit 14 by a releasable connection 15. A reference external electrode 16, adapted to be secured to an exterior portion of the patient, such as the patient's abdomen or thigh by suitable adhesive, has an elongated shaft 17 with a proximal end 18 secured to the pH monitoring unit 14 by a releasable connection 19. The reference electrode is preferable a silver/silver chloride electrode. A suitable pH sensing electrode system is the Zinetics 24ME multi-use pH catheters from Medtronic, Inc.

The pH monitoring unit 14 includes a personal digital assistant 20, such as the Palm Pilot with a data acquisition system 21, such as a DataStick DAQ adapter. Shafts 12 and 17 are secured to the manifold 22 by releasable connections 15 and 19 and transmission line 23 leads from the manifold 22 to a receiving port of the data acquisition system 21 to transmit the voltage differential between the active electrode 11 and the reference electrode 16.

The pH monitoring system 10 includes an introducing sheath 24 which is configured to extend through the patient's vaginal canal and into the uterine cavity. The distal end 25 of sheath 24 is preferably provided with a tapered non-traumatic tip. The proximal end 26 has a collar 27, an attached spring 28 and Toughy-Borst adapter 29 secured to the proximal end of the spring 28 and configured to be releasably secured to the exterior of the shaft 12 of the active electrode 11.

FIGS. 2 and 3 illustrate in greater detail the introducer sheath 24. The sheath 24 has an elongated shaft 32 with an inner lumen 33 configured to slidably receive the active electrode 11 and shaft 12 thereof, and a discharge port 34 at the distal end 25 of the sheath. The proximal end of the sheath has a pair of tabs or eyelets 35 for securing the proximal end to the patient, e.g. the patient's uterine cervix or vaginal labia, by a clip or suture or other suitable means.

Figure 4:
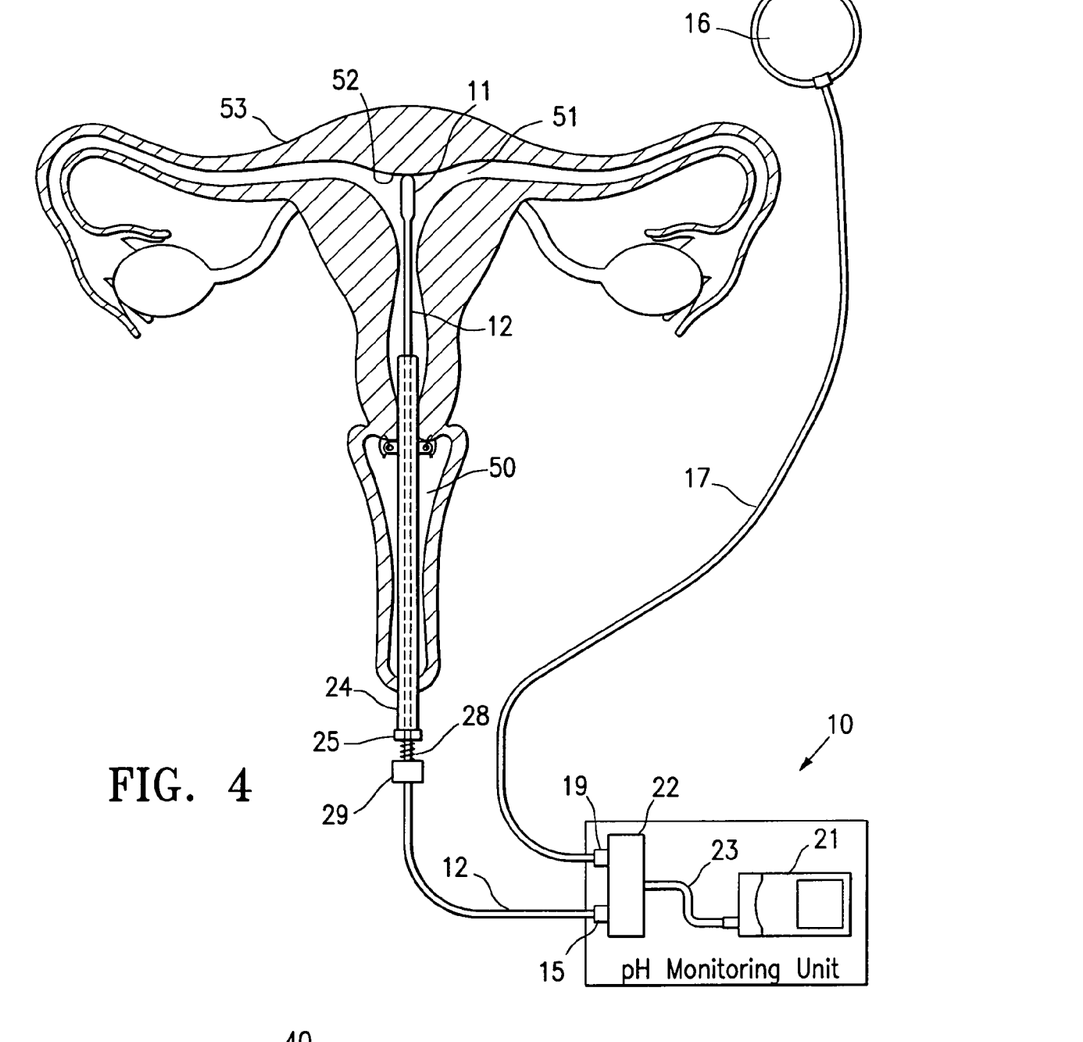
FIG. 4 is a schematic illustration of a female patient's reproductive organs with a component monitor shown in FIG. 1 deployed within the patient's uterine cavity.

As shown in FIG. 4, the active electrode 11 on the distal end of the shaft 12 is introduced into the patient's vaginal canal 50, advanced into the uterine patient's uterine cavity 51 until the active electrode 11 is pressed against the endometrial fundus 52 of the patients uterus 53 to monitor the pH of the endometrial tissue. After the sheath is secured to the patient, the Toughy-borst adapter 29 on the sheath 24 is pulled proximally to elongate the spring 28 and then tightened about the exterior of the shaft 12. The biasing action of the spring 28 urges the shaft 12 further into the patient's uterine cavity 51 and presses the active electrode 11 against the fundus 52 to ensure proper contact for pH detection of the endometrial lining of the patient's uterus 53.

An exterior reference electrode 16 is secured to the patient's skin at a convenient place close to the patient's vaginal opening, e.g. the abdomen or thigh. The active electrode shaft 12 and the reference electrode shaft 17 are operatively connected to the manifold 22 of the monitor unit 14 at releasable connections 15 and 19 respectively. The electrical signals received from the active electrode 11 through conductor 37 and reference electrode 16 through conductor 38 are transmitted to the data acquisition system 21 through transmission line 23. The endometrial tissue pH is displayed on the PDA.

Figure 5:
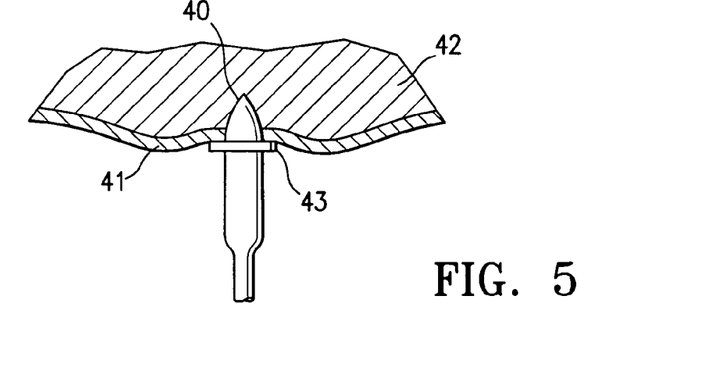
FIG. 5 is a schematic view illustrating a monitoring electrode extending into a patient's myometrium.

As shown in FIG. 5, the active electrode 40 may be configured to penetrate the uterine wall through the endometrial layer 41 into the myometrial layer 42. The pH signals tend to be a little more stable. However, a coller 43 should be provided to limit the penetration into the myometrial layer to prevent penetration through the uterine wall.

In some instances it may be desirable to provide an active electrode with a radio transmitter which can be implanted into the uterine wall without a catheter extending out of the patient's vaginal canal. A monitor is provided with a suitable receiver to receive the signal from the active electrode transmitter and display or record the received signal as a function of the pH (or other component parameter). This allow for the use of a uterine artery clip or clips such as described in co-pending application Ser. No. 01/113,096, filed on Mar. 28, 2002 and Ser. No. 10/300,495, filed on Nov. 19, 2002, both of which have been assigned to the present assignee Vascular Control Systems, Inc. The clips may be applied to occlude the patient's uterine artery with the pH monitor system installed to allow the patient sufficient mobility to leave the clinical setting without a catheter extending out o the patient's vaginal canal and return when the pH monitor indicates that the uterine artery has been occluded long enough so that the uterine clip should be removed. The active electrode and transmitter may also be removed.

The temporary occlusion of uterine arteries for the treatment for uterine fibroids and uterine bleeding from a variety of causes and the monitoring of the concentration of components, e.g. pH, in the uterine tissue environment can be effective. The procedure is illustrated in the following example.

EXAMPLE

Figure 6:
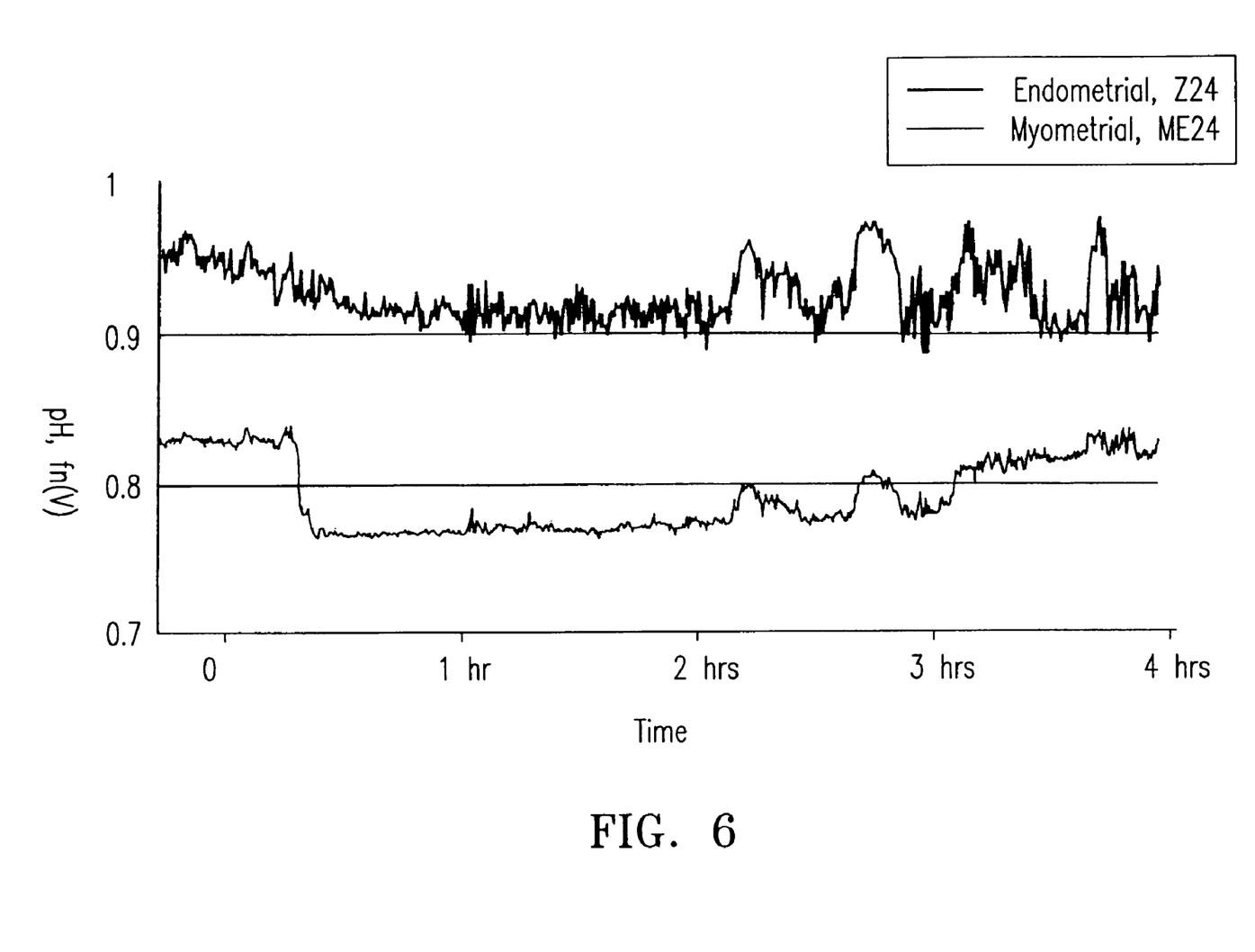
FIG. 6 is a graph illustrating the pH changes to endometrial tissue and myometrial tissue due to uterine artery occlusion over a period of time.

Ten women with menorrhagia, pelvic pain or pressure, and/or anemia had myomas and uterus larger than 13 weeks gestation were subjected to bilateral uterine artery occlusion. Prior to the uterine artery occlusion a pH monitoring probe (Zinetics 24ME multi-use pH catheter) was placed transcervically into the endometrium and myometrium. Before uterine artery occlusion, the uterine tissue pH value for the 10 patients averaged 6.7 pH units, ranging from 6.4 to 6.9. The average decline in pH during the initial phase was 0.5 pH units, ranging from 0.4 to 0.6. The uterine tissue of all of the patients exhibited a similar pattern of pH value changes over the monitoring period (less than 24 hours). The initial phase occurred over a period of about 5 to about 150 minutes, averaging 32 minutes. The pH of uterine lining tissue declined an average of about 0.5 pH units during the initial phase. In the dwell phase, the pH levels of the uterine tissue remained at essentially the reduced levels over a period of about 5 to about 150 minutes, averaging 53 minutes. In the return phase, the pH returned to the preocclusion levels from the low pH levels of the dwell phase over a period of about 30 to about 180 minutes, averaging about 114 minutes. A typical display of the variation of pH of the endometrial and myometrial tissue with respect to time due to the ischemic effects of uterine artery occlusion is illustrated in FIG. 6.

While particular forms of the invention have been illustrated and described herein, it will be apparent that various modifications and improvements can be made to the invention. For example, while a porous antimony electrode was described as an active electrode a variety of electrodes may be used. Moreover, the reference electrode is described herein as being attached to the exterior of the patient. However other reference electrode locations may be employed. For example, the shaft of the monitoring system may have the active electrode and a reference electrode.

Individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety. Accordingly, it is not intended that the invention be limited, except as by the appended claims.

What is claimed is:

1. A transvaginal device for measuring the pH of a female patient's uterine tissue, comprising:
    a. a first elongated shaft which is configured to extend through the female patient's vaginal canal and which has proximal and distal ends, a first port in the proximal end, a second port in the distal end and an inner lumen extending within the shaft in fluid communication with the first and second ports; and
    b. a second elongated shaft which is configured to be slidably disposed within the inner lumen of the first elongated shaft, which has a proximal end and a distal end, which has an active electrode at the distal end of the shaft configured to sense an electrical parameter representing pH of the patient's uterine tissue and to generate a signal representing the sensed parameter and which is configured to transmit the signal from the active electrode representing the pH; and
    c. a resilient interconnection between the first and second elongated shafts which has a biasing mechanism to urge the second elongated shaft distally with respect to the first elongated shaft to facilitate slidable motion therebetween and configured to extend the distal end of the second shaft distally beyond the distal end of the first shaft to ensure that the active electrode on the distal end of the second shaft engages uterine tissue.

2. The device of claim 1, wherein the first elongated shaft is an introducer sheath.

3. The transvaginal device of claim 1, wherein the active electrode is a porous electrode.

4. The transvaginal device of claim 1, wherein the active electrode is an antimony based half cell electrode.

5. The transvaginal device of claim 1, including a reference electrode.

6. The transvaginal device of claim 5, wherein the reference electrode is a silver/silver chloride half cell.

7. The transvaginal device of claim 1, wherein the second elongated shaft has an electrical conductor which has one end electrically connected to the active electrode and which is configured for transmitting an electrical signal representing the voltage sensed by the active electrode.

8. The transvaginal device of claim 7 including a reference electrode which is configured to be secured to an exterior location on the patient and sense voltage and a signal transmitting member connected to the reference electrode for transmitting a signal representing the voltage sensed by the reference electrode.

9. The transvaginal device of claim 1, wherein the second elongated shaft is provided with a transmitter to transmit a signal from the active electrode representing a uterine tissue parameter to the pH monitor which converts the signal to a pH value.

10. The transvaginal system of claim 8, including a manifold which develops a signal representing a difference between voltage sensed by the active electrode and voltage sensed by the reference electrode which is a measure of the pH of the uterine tissue.

11. The transvaginal device of claim 1 including a reference electrode which is located on the shaft proximal to the active electrode.

12. The transvaginal device of claim 1, wherein the first elongated shaft is configured to provide access to the patient's uterine cavity and is configured to be secured at least in part to the patient.

13. The transvaginal device of claim 12, wherein the first elongated shaft is in part configured to be secured within the patient's vaginal canal.

14. The transvaginal device of claim 1, wherein the biasing mechanism is configured to be releasably secured to the second elongated shaft.

15. The transvaginal device of claim 14, wherein a Toughy-Borst adapter is provided on a proximal end of the biasing mechanism to releasably secure the proximal end of the biasing mechanism to the second elongated shaft so as to urge the second elongated shaft distal to the first elongated shaft.

16. The transvaginal device of claim 1, wherein the biasing mechanism is a spring.

17. The device of claim 1, wherein the second elongated shaft is a pH measuring catheter.

18. The transvaginal device of claim 1, wherein the active electrode senses voltage.

19. The transvaginal device of claim 18, wherein a reference electrode senses voltage.

20. The transvaginal device of claim 19 including a manifold configured to compare the signal from the active electrode with the signal from the reference electrode.

21. The transvaginal device of claim 20, wherein the manifold generates a signal representing the difference between the signal from the active electrode and the signal from the reference electrode.

22. An assembly for monitoring the pH of a female patient's uterine tissue, comprising:
   a. an elongated introducer sheath which has proximal and distal ends, a first port in the proximal end, a second port in the distal end and an inner lumen extending within the sheath in fluid communication with the first and second ports, and which is configured to be slidably disposed about the elongated shaft; and
   b. an elongated shaft which is slidably disposed within the inner lumen of the introducer sheath, which has a distal end with a uterine tissue engaging electrode configured to sense an electrical parameter relating to the pH of the patient's uterine tissue and a proximal end configured to extend out of a patient's vaginal canal, and which has an electrical conductor configured to transmit a signal from the electrode representing the sensed electrical parameter to a pH monitoring unit; and
   c. a biased interconnection between the elongated shaft and the introducer sheath to urge the elongated shaft distally with respect to the introducer sheath.

23. The assembly of claim 22, wherein the tissue engaging electrode is an active electrode.

24. The assembly of claim 23 having a reference electrode which is configured to be secured to an exterior location of the patient.

25. The assembly of claim 24, wherein the reference electrode is a silver/silver chloride half cell.

26. The assembly of claim 23, wherein the tissue engaging electrode is a porous electrode.

27. The assembly of claim 23, wherein the tissue engaging electrode is an antimony based half cell electrode.

28. The assembly of claim 23, wherein the elongated shaft is electrically connected to the pH monitoring unit by an electrical conductor for transmitting an electrical signal representing the voltage sensed by the tissue engaging electrode.

29. The assembly of claim 28, including a reference electrode which is configured to be secured to an exterior location of the patient and a connected signal transmitting member for transmitting a signal representing the voltage sensed by the reference electrode.

30. The assembly of claim 29, wherein the pH monitoring unit includes a manifold which develops a signal representing a difference between voltage sensed by the tissue engaging electrode and voltage sensed by the reference electrode which is a measure of the pH of the uterine tissue.

31. The assembly of claim 23, wherein the elongated shaft is provided with a transmitter to transmit a signal from the tissue engaging electrode representing a uterine tissue parameter to the pH monitoring unit which converts the signal to a pH value.

32. The assembly of claim 23, wherein the elongated introducer sheath is configured to provide access to a patient's uterine cavity and is configured to be secured at least in part to the patient.

33. The assembly of claim 24, wherein the elongated introducer sheath is in part configured to be secured within a patient's vaginal canal.

34. The assembly of claim 23, having a biasing mechanism interconnecting the elongated shaft and the elongated introducer sheath to urge the elongated shaft distally with respect to the introducer sheath to ensure that the tissue engaging electrode on the distal end of the elongated shaft engages tissue within the uterine cavity.

35. The assembly of claim 34, wherein the biasing mechanism is configured to be releasably secured to the elongated shaft.

36. The assembly of claim 35, wherein a Toughy-Borst adapter is provided on a proximal end of the biasing mechanism to releasably secure the proximal end of the biasing mechanism to the elongated shaft.

37. The assembly of claim 34, wherein the biasing mechanism is a spring.

38. A device for monitoring a component of a female patient's uterine tissue, comprising:
   a. a first elongated shaft which is configured to extend through the female patient's vaginal canal, uterine cervix and into the uterine cavity of the female patient's uterus and which has proximal and distal ends, a first port in the proximal end, a second port in the distal end and an inner lumen extending within the shaft in fluid communication with the first and second ports; and
   b. a second elongated shaft which is configured to be slidably disposed within the inner lumen of the first elongated shaft, which has a proximal end and a distal end, which has an active electrode at the distal end of the shaft configured to sense the component concentration in the patient's uterine tissue and to transmit a signal representing the component concentration to a pH monitoring unit;
   c. an interconnection between the first and second elongated shafts which has a biasing mechanism to urge the second elongated shaft distally with respect to the first elongated shaft to facilitate slidable motion therebetween and configured to extend the distal end of the second shaft distally beyond the distal end of the first shaft to ensure that the active electrode on the distal end of the second shaft engages uterine tissue.

39. The device of claim 38, wherein a reference electrode is configured to be held in contact with the patient's body to generate a reference signal for comparison with the signal representing the component concentration in the tissue environment.

40. The device of claim 39, wherein the pH monitoring unit has a manifold configured to generate a difference signal between the reference signal and the signal from the active electrode.

41. The device of claim 28, wherein a conductor is provided to transmit the difference signal to a data acquisition system of the pH monitoring unit.

42. The device of claim 38, wherein the first elongated shaft is an introducer sheath.

43. The device of claim 38, wherein the second elongated shaft is a component monitoring catheter.

44. A transvaginal device for monitoring the pH of a female patient's uterine tissue comprising:
   a. an elongated introducer sheath which has proximal and distal ends, a first port in the proximal end, a second port in the distal end and an inner lumen extending within the sheath in fluid communication with the first and second ports;
   b. an elongated shaft slidably disposed within the elongated introducer sheath which has a distal end, a tissue penetrating electrode on the distal end configured to sense an electrical parameter of the tissue and to generate a signal representing the sensed electrical parameter, and a proximal end configured to extend out of a patient's vagina when the tissue penetrating electrode is placed against a patient's uterine wall; and
   c. a biased interconnection between the elongated shaft and the introducer sheath to urge the elongated shaft distally with respect to the introducer sheath.

45. The transvaginal device of claim 44, wherein the biasing mechanism is configured to be releasably secured to the elongated shaft.

46. The transvaginal device of claim 45, wherein a Toughy-Borst adapter is provided on a proximal end of the biasing mechanism to releasably secure the proximal end of the biasing mechanism to the elongated shaft.

47. The transvaginal device of claim 46, wherein the biasing mechanism is a spring.

48. The transvaginal device of claim 44, wherein the tissue penetrating electrode is an active electrode.

49. The transvaginal device of claim 48, wherein the elongated shaft is configured to transmit a signal from the tissue penetrating electrode to a pH monitoring unit.

50. The transvaginal device of claim 48 having a reference electrode which is configured to be secured to an exterior location on a patient's body.

51. The transvaginal device of claim 50, wherein the reference electrode is a silver/silver chloride half cell.

52. The transvaginal device of claim 48, wherein the tissue penetrating electrode is a porous electrode.

53. The transvaginal device of claim 49, wherein the elongated shaft is provided with a transmitter to transmit a signal from the tissue penetrating electrode representing a uterine tissue parameter to the pH monitoring unit which converts the signal to a pH value.

54. The transvaginal device of claim 49, wherein the elongated shaft is electrically connected to the pH monitoring unit by an electrical conductor for transmitting an electrical signal representing the voltage sensed by the tissue penetrating electrode.

55. The transvaginal device of claim 54, including a reference electrode which is configured to be secured to an exterior location on a patient's body and a connected signal transmitting member for transmitting a signal representing the voltage sensed by the reference electrode.

56. The transvaginal device of claim 55, wherein the pH monitoring unit includes a manifold which develops a signal representing a difference between voltage sensed by the tissue penetrating electrode and voltage sensed by the reference electrode which is a measure of the pH of the uterine tissue.

57. The transvaginal device of claim 48, wherein the tissue penetrating electrode is an antimony based half cell electrode.

58. The transvaginal device of claim 44, wherein the elongated introducer sheath is configured to provide access to a patient's uterine cavity and is configured to be secured at least in part to the patient.

59. The transvaginal device of claim 58, wherein the elongated introducer sheath is in part configured to be secured within a patient's vaginal canal.

* * * * *